United States Patent
Alaca et al.

(10) Patent No.: US 10,458,865 B2
(45) Date of Patent: Oct. 29, 2019

(54) MULTI-AXIS PIEZORESISTIVE FORCE SENSOR

(71) Applicant: Koc Universitesi, Sariyer, Istanbul (TR)

(72) Inventors: Burhanettin Erdem Alaca, Istanbul (TR); Halil Bayraktar, Istanbul (TR); Onur Aydin, Istanbul (TR)

(73) Assignee: KOC Universitesi, Istanbul (TR)

( * ) Notice: Subject to any disclaimer, the term of this patent is extended or adjusted under 35 U.S.C. 154(b) by 142 days.

(21) Appl. No.: 15/679,726

(22) Filed: Aug. 17, 2017

(65) Prior Publication Data

US 2017/0343431 A1 Nov. 30, 2017

Related U.S. Application Data

(63) Continuation of application No. PCT/TR2015/000082, filed on Feb. 18, 2015.

(51) Int. Cl.
| | |
|---|---|
| *G01L 1/18* | (2006.01) |
| *B81B 3/00* | (2006.01) |
| *G01L 1/22* | (2006.01) |
| *G01N 15/10* | (2006.01) |
| *G01N 33/483* | (2006.01) |

(52) U.S. Cl.
CPC .............. *G01L 1/18* (2013.01); *B81B 3/0021* (2013.01); *G01L 1/22* (2013.01); *G01N 15/10* (2013.01); *G01N 33/4833* (2013.01); *G01N 2015/1006* (2013.01)

(58) Field of Classification Search
None
See application file for complete search history.

(56) References Cited

U.S. PATENT DOCUMENTS

| | | | | |
|---|---|---|---|---|
| 4,483,203 A | * | 11/1984 | Capper | G01G 3/1402 73/862.01 |
| 8,250,927 B2 | * | 8/2012 | Anand | G01B 7/20 73/763 |
| 9,261,423 B2 | * | 2/2016 | Benfield | G01L 5/162 |
| 2005/0034529 A1 | | 2/2005 | Tang et al. | |
| 2010/0199783 A1 | * | 8/2010 | Sakurai | G01L 5/161 73/862.044 |
| 2014/0260653 A1 | * | 9/2014 | Merrell | G01L 1/16 73/774 |
| 2015/0075250 A1 | * | 3/2015 | Kosa | G01L 5/162 73/1.15 |

OTHER PUBLICATIONS

International Search Report of the International Searching Authority, dated Oct. 12, 2015, pp. 1-3, issued in International Application No. PCT/TR2015/000082, European Patent Office, Rijswijk, The Netherlands.

Written Opinion, dated Oct. 12, 2015, pp. 1-5, issued in International Application No. PCT/TR2015/000082, European Patent Office, Rijswijk, The Netherlands.

* cited by examiner

*Primary Examiner* — Andre J Allen
(74) *Attorney, Agent, or Firm* — Brinks Gilson & Lione

(57) ABSTRACT

A microelectromechanical system (MEMS) sensor device comprising at least one microelectromechanical system sensor to characterize intracellular dynamics and behavior of a living biological cell so as to quantitatively measure the mechanical strength thereof. The microelectromechanical system sensor being responsive to mechanical force changes during said cell's contraction, migration, proliferation and differentiation.

17 Claims, 2 Drawing Sheets

MULTI-AXIS PIEZORESISTIVE FORCE SENSOR

PRIORITY

This application is a continuation of International Patent Application No. PCT/TR2015/000082 filed Feb. 18, 2015, which is herein incorporated by reference in its entirety.

TECHNICAL FIELD

The present disclosure relates to a multi-axis piezoresistive force sensor array and methods of measuring the mechanical behavior of biological cells.

BACKGROUND

Microelectromechanical systems (MEMS) technology enables the fabrication and utilization of miniaturized force sensor devices that can be designed to have direct contact with biological cells and conduct force measurements in the micronewton and sub-micronewton ranges. Piezoresistive nanowires enable the design of sensors capable of very sensitive measurements of displacement and mechanical force with a level of miniaturization that is not possible with other methods of transduction such as capacitive or optical sensing. The level of miniaturization makes it possible to carry out contact force measurements on single biological cells.

SUMMARY

Cells interact with each other under the action of chemical and mechanical forces during the formation of tissues and organs, and to maintain biological functions in the organism. The cellular forces play a key role if any changes occur in many physiological environments. Cells generate and are exposed to externally applied forces from the extracellular matrix that is essential for carrying the information to the neighboring cells. Other forces such as shear stress, compression around the tissue, and topography change around the cell can be transmitted directly to the cells and cause deformations and rigidity change in the cells. Stress induces the alteration of biological signals and cells undergo very fast changes both at structural and molecular level. Cell dividing, reorganization of cellular matrix and differentiation are observed as response to the mechanical stimuli via chemical and biological alteration in the cell. For instance, the differentiation of mesenchymal stem cells into neuronal cells was favored in the presence of soft matrices whereas myogenic differentiation and osteogenic differentiation was observed in semi rigid and very stiff materials, suggesting that passing of information is only possible when these changes take place in a systematic fashion of the medium's matrices around the stem cells.

Any slowing or disarray in the transfer of mechanical forces triggers uncontrolled cellular incidents and leads to many physiological problems and fatal diseases. For example, axon and dendrite growth from the surface of a neuron plays an important role in cellular communication during the early phase of neurological development. It is very important to understand effects that different neurons have on each other during this development. Similarly, in later years structural changes in neurons are believed to lead to various neurological malfunctions such as Parkinson and Alzheimer.

Intermediate filaments—in addition to microtubules and microfilaments—are one of the building blocks of cytoskeleton of eukaryotic cells, especially neurons. Until recently it was believed that the function of intermediate filaments was purely structural. However, intermediate filaments are the main cytoskeleton members responsible for the transfer of mechanical stimulus from the cell membrane to the nucleus and hence they are the critical members that determine cell's response to any mechanical stimulus. As a natural consequence, new findings indicate that intermediate filaments play a critical role in mechanical function and response of cells. The spatiotemporal role of the filaments as structures for organizing mechanical tension within the cell determines tissue morphogenesis. Similar mechanical changes also dramatically change neuronal functions. For example, the degradation of axons after head injury occurs due to explosion or car accidents. The sensitive devices are required to monitor axonal growth in the presence of small molecules.

The growth and organization of the cell tissue rely on tensions present during embryonic development. The role of vital physical forces on the synthesis of structural proteins and their self-assembly and function has been poorly understood. Without the physical force and stimulus, the cells undergo apoptosis and do not maintain their important functions. The changes of matrix around the cell cause diseases such as cancer metastasis due to changes of flow near the cancer regions, the reduction of lung capacity, and smaller alveoli in the lungs are all the cause of structural and physical changes in the cells. It was also demonstrated that benign cells are more rigid compared to cells at a metastatic stage. The pathogenesis at a cellular level can be determined if the acting forces are localized over the cell surface and magnitude of force is determined sensitively. For example sickle cell anemia causes a decrease of the stiffness of red blood cells. The mechanical properties of red blood cells are vital for the delivery of oxygen to organs and tissues. They have bioconcave and highly elastic structures. The similar mechanical changes were also observed after the infection of the red blood cells by a malaria parasite. The stage of diseases and diagnosis can be determined by quantitatively measuring the mechanical strength of the cells.

To characterize the cells' mechanical properties and understand sensing mechanism of force acting on cells, the detailed analysis and high throughput quantitative screening of many cells are needed. Mechanisms such as the modulation of cellular functions can be elucidated quantitatively. Despite the importance of mechanical force in biological processes, several examples of relationship between the forces and the resulting biological outcome are demonstrated in several latest studies. However, the predictions of the biological changes after an external stress are not well understood and cannot be elucidated explicitly. The force magnitudes and cell dimensions being very small, they require development of new approaches for sensitive measurement at micro/nano-scale.

An emerging platform to study cellular mechanobiology is microelectromechanical systems (MEMS) that are widely used to measure the displacement and applied forces with micronewton resolution. Even though the magnitude of change in cells is currently far lower than the capabilities of these micro engineered devices, the alternatives and sensitive MEMS tools, devices can be designed since the methods in microfabrication technology is well-established in terms of device design, manufacturing and characterization of devices.

Current measurements of physical properties and behavior of biological cells are primarily performed under a fluorescence or wide light microscopy imaging systems. Cells' physical response to external stimuli is frequently difficult to visualize in real time microscopy. The tasks of cell culture, monitoring, labeling and manipulation can be tedious and time consuming.

Microscope imaging systems are mainly used to determine the physical properties of cells as well as intracellular dynamics of macromolecules. However the force measurement under external stress is difficult to visualize at high spatiotemporal resolution. It is very time consuming method and often suffers from slow processing time during the video acquisition and after image processing.

To understand the physical strength of cellular membrane and stress on cells, the deformation of the cellular membranes were initially studied using different micromanipulation tools. They are used to mechanically stretch cells and study the tensile strength or stiffness change of the cell. Mechanical or optical techniques are still commonly used to apply controlled mechanical forces to living cells and tissues. The most advanced tools to apply force are micropipette aspiration, laser trapping and magnetic probes.

A calibrated device at a given force and stress conditions are used to quantify the mechanical properties of individual cells. Micropipette technique is a highly suitable method to determine the viscoelastic properties such as elastic modulus or viscosity of the cells. Briefly, to deform a portion of a single cell, a negative pressure is applied that elongates the cell wall in parallel to the direction of force. Aspiration length and negative pressure has to be measured to determine the stiffness of the cell. Typically, the magnitude of the pressure changes from 1-5 Pa to 1-2 kPa for soft and stiff cells respectively. Typically 100 pN to 0.1 µN of force is applied to deform the cells. The friction forces are typically ignored in these calculations. On the other hand, the characterization of local forces/deformation is quite difficult due to local deformation and the complexity of mixed strained force. An advanced manipulation method is known as laser tweezer.

To measure the local deformation, fluorescent bead molecules were locally adhered to the surface of cell membrane by small ligands, antibodies or other electrostatic interactions. The force that localized the particle at a given position is adjusted through the laser power that depends on the local properties of the cell membrane. Using optical traps at high laser powers, it can be generated 0.1-5 nN of forces. However, long time exposure of cells by high laser beams cause damage to the cell surface and induce non-specific deformation on the cell surface. The method is suitable to measure forces at a single cell level. The analysis of many cells requires other methods.

Another widely used class of methods is the microelectromechanical systems that include the cantilever sensors, force sensors and flow sensors. For example, AFM tips are used to measure forces as low as 1 pN up to 10 nN. In AFM, a vertical microcantilever moves over the cell to deform the cellular membrane. Based on the deflection of the cantilever, the local stiffness of the cell is measured to distinguish whether the stiffness of a cell is varied over the entire cell surface under certain conditions. Therefore, a map of cell's rigidity across the cell surface can be generated. However the use of AFM requires sensitive, expensive and bulky optical instrumentation. The applicability of AFM is very difficult for different applications.

Microfabricated micropost arrays have been used to measure forces exerted by the adhesion sites of the individual cells. The small posts also called nanopillars that are made from silicone polymer were used to track changes due to structural changes of cells because they are highly elastic. The movement of nanopillars is followed by light microscopy. The deflection of the posts is monitored that are directly proportional with local forces. Young's modulus of the polymer material is used to calculate the total force. Direct and distinct relationships between cellular traction force and cell spreading area are demonstrated in several cells such as fibroblasts, endothelial cells, epithelial cells, and smooth muscle cells.

There are several disadvantages of using nanopillars to measure cellular forces. First, cell adhesion may change due to the pattern of the nanoposts, therefore possibly causing unrelated stress over the entire cell. Secondly, the deflection of each post is visualized by light microscopy that restricts its use for imaging other events in the cell simultaneously. To overcome such problems, the cellular force has to be measured independently; therefore the microscope can be used to image protein dynamics in the cell.

Microelectrode arrays that exert an electric field over the cell surface are used to study cell deformation in different mediums. The polarization of cell's membrane is modulated by modulating the strength of electric field near the surface. Red blood cells were studied by this method. However the cell membrane can be easily ruptured if excessive voltage is applied to the medium.

The use of mass loading sensor based on MEMS is highly suitable, having features with dimensions less than 5-10 µm in at least one dimension, sensitivity to mechanical force, and dramatically lower averaging time during the signal processing from MEMS device.

The measurement of cell's mechanical behavior on substrates and physical properties using microscopy systems is very difficult that requires sample handling. The present invention therefore overcomes the many problems associated with visualizing cell responses under stress. Many cells can be analyzed in parallel using an array of multi-axis sensors. It is superior to the other devices that allow single cell measurements. Many of the force measurements of cells are capable of applying small force to a single cell. The probe in accordance with the disclosure has an advantage over these methods due to the fact that array type parallel multiplex analysis can be performed.

The image of the protein distribution can be monitored in parallel during the force measurement. As mentioned above, the physical deformation and response of cells due to external stimuli can be measured using multi-axis sensor and enhance the measurements available from light microscopy systems.

The method/device describes an advantageous approach and sensitivity to detect force levels down to 100 nN, these levels are extremely small and no established method has been demonstrated so far. The available technologies that are currently effective in measuring forces in the range of 100 µN or higher are typically used for haptic applications. However, unlike engineered materials such as metals, ceramics, and polymer systems, biological cells have integrated and highly complex living systems. The integration with other systems such as fluorescence microscopy may be required to elucidate the mechanism of the system. To monitor the transduction of mechanical signal into biochemical signal, the pathways may need to be studied using fluorescence imaging methods. Nonetheless, small and sensitive sensing systems have to be adapted to perform dynamic and contact measurements of different biological processes such as cell movement, contraction, proliferation and migration. The method is minimally invasive to the cell.

According to the disclosure, the dynamic changes of intermediate filaments and force distribution in neutrophils is characterized to monitor the degradation and formation changes of filament structures and its effect on force distribution. These cells do not show any polarization at rest in the presence of chemical stimulus. According to the present disclosure, a small size sensor array provides multiplex analysis of many cells on a single device.

The resolving capacity of MEMS device can measure as low as 1-10 nanonewtons of forces to determine the mechanical behavior of single cells as well as multi cell complex systems. The micrometer size of most mammalian cells has a good match with the MEMS platform, therefore providing a high spatial and temporal resolution.

An interesting feature is to provide a piezoresistive sensor array for measuring the electric current flow through a nanowire that is proportional to in-plane force gradients exerted parallel to the surface of a mechano-sensitive platform attached via nanowires.

Another interesting feature is to provide a piezoresistive sensor array to measure in-plane force gradients from many biological cells using a time-domain multiplexer.

Other features include the microfabrication and electromechanical characterization of piezoresistive nanowires.

Piezoresistive devices and transducers can be designed to measure small changes in force magnitude. The system and method comprises several steps such as device fabrication, calibration, and testing with biological cells.

According to a first aspect, a method of fabricating the multi-axis MEMS sensor is provided. A method includes the steps of simulation of various features, masks for lithography and providing the details of microfabrication. The signal lines of pixels in the sensors are being arranged independently therefore the data can be obtained separately from different pixels.

Another aspect describes the calibration of the device and its integration with microscopy imaging systems. The fluorescent imaging systems to measure physical properties of cells is very difficult due to photobleaching of fluorophore used as a marker that decrease the observation time and also high toxicity if they are expressed at high concentrations. When it is used to determine the force and stress distribution in the cell, it limits to monitor the intracellular dynamics. A method is provided to image the cellular physical changes by the change of resistance of piezoresistive nanowire. It is a label-free imaging method. Therefore it reduces the sample preparation procedures that are very tedious and time consuming. Another advantageous feature of piezoresistive force sensor is small size.

TA method of and system for characterizing dynamics changes of a biological cell is described. The method and system may be used to measure in-plane mechanical contact forces down to nanonewton range, such as for instance within the range of 100 nN-10 μN. To achieve dynamics and contact measurements of basic biological processes in cells, a micro/nano sensing system can be used to measure small changes in force. The mechanical force changes during a cell's contraction, migration, proliferation and differentiation is hence measured at nanonewton levels.

The design and fabrication of an improved MEMS force sensor device that uses piezoresistive Silicon nanowires as electromechanical transducer elements for the sensing of applied mechanical force is described. Piezoresistivity is an electromechanical effect where mechanical stress induces a change in the material's electrical resistivity. Single crystal Silicon—which is the workhorse of micro & nanofabrication processes—, is known to exhibit piezoresistive properties.

Diffused piezoresistors have been used in the past in pressure sensors and cantilever type sensors. A MEMS force sensor device that utilizes piezoresistive Silicon nanowire transducers is presented.

The disclosure therefore relates to a method of and system and device to characterize the intracellular dynamics and behavior of at least one biological cell. The device can be used to measure the small displacements on the mechano-sensitive platform. The device is configured to have a direct contact with living cells. The method provides a device with an array format therefore at least one biological cell can be characterized when the contact is established. The device provides microscale study of tissue components as well as the individual cells.

The miniaturized technology can be integrated with fluorescence microscope systems and hence provides a simultaneous data collection from both platforms. The disclosure describes the methods of using multi-axis piezoresistive force sensors to demonstrate the changes in intermediate filaments in living cells. While the role of intermediate filaments is studied, collective behavior of other building blocks and intricate cellular deformation can also be quantified.

Therefore, a fully integrated, miniaturized piezoresistive MEMS force sensor that measures forces generated by living cells is demonstrated. The MEMS sensor fabrication, calibration and cell attachment of which is demonstrated is fabricated using a deep etching process. The sensor measures forces as small as 100 nN. A method of characterizing the behavior of one cell is described.

BRIEF DESCRIPTION OF THE FIGURES

Accompanying drawings are given solely for the purpose of exemplifying a multi-axis piezoresistive force sensor and a method for manufacturing the same, whose advantages over prior art were outlined above and will be explained in brief hereinafter.

The drawings are not meant to delimit the scope of protection as identified in the claims nor should they be referred to alone in an effort to interpret the scope identified in said claims without recourse to the technical disclosure in the description of the present systems and methods.

DETAILED DESCRIPTION

Figure 1:
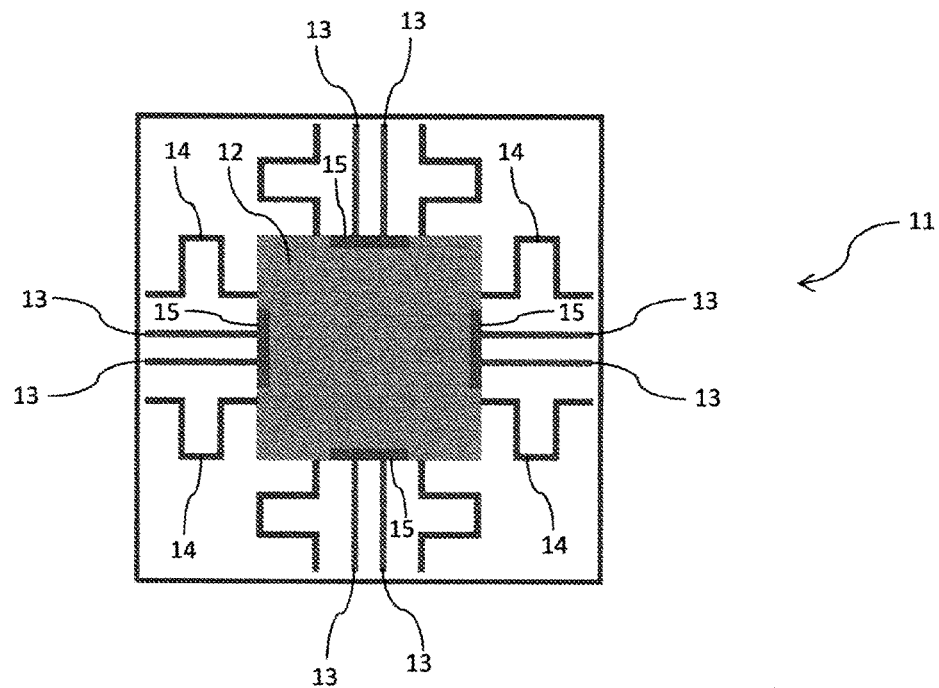
FIG. 1 demonstrates a general schematic view of a MEMS sensor comprising an interaction platform, piezoresistive nanowires, and retaining springs.

The present disclosure proposes a piezoresistive sensor and array of sensors for measuring in-plane contact forces. According to the disclosure, a MEMS (Microelectromechanical system) force sensor (11) is composed of an interaction platform (12), strain-sensitive nanoscale elements (13) in the form of piezoresistive nanotubes or nanowires, and retaining springs (14). FIG. 1 shows the schematic of the device design including the components.

The interaction platform (12) is suspended by the strain-sensitive nanoscale elements (13) and retaining springs (14) which bridge between the interaction platform (12) and respective anchoring means. The interaction platform (12) can move under the action of external forces. It is the component that the biological cell interacts with and exerts forces on. The strain-sensitive nanoscale elements (13) (of silicon) are used as electromechanical transducers to measure the displacement of the interaction platform (12) due to the forces exerted on it by the biological cells. The motion of the interaction platform (12) generates mechanical stress in the strain-sensitive nanoscale elements (13). This stress induces changes in a strain-sensitive nanoscale element's (13) resistivity, and hence its electrical resistance, due to the piezoresistive properties of doped single crystal silicon. The change in resistance of the strain-sensitive nanoscale element (13) can be monitored by current-voltage (I-V) measurements, allowing the computation of the force exerted on the interaction platform (12) by the biological cells.

Figure 2:
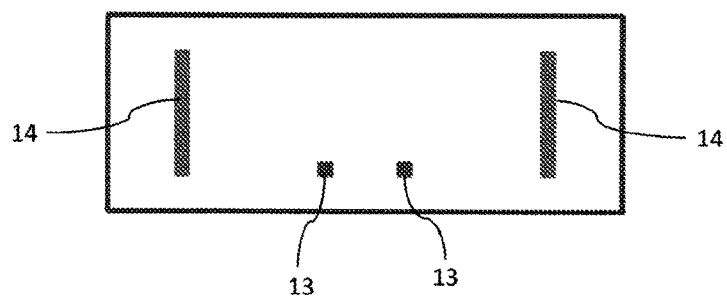
FIG. 2 provides a schematic cross-sectional view of a MEMS sensor demonstrating the cross-section of the retaining springs and position of the piezoresistive nanowires.

The function of the retaining springs (14) is to constrain the motion of the interaction platform (12) to in-plane displacements. When a force is applied to the surface of the interaction platform (12), a bending moment is generated due to the distance between the surface of the interaction platform and its center of gravity. This bending moment causes a tilting motion of the platform, and the strain-sensitive nanoscale elements (13) bend as a result. Bending of a strain-sensitive nanoscale element (13) causes a non-uniform stress distribution, which reduces the sensitivity of the piezoresistive nanowire transducers. Maintaining a uni-axial stress state (tensile or compressive) on the strain-sensitive nanoscale elements (13) is important to maximizing the sensitivity of the MEMS force sensor (11). To this end, said retaining springs (14) are used to prevent the tilting of the interaction platform (12) under applied bending moments. The retaining springs (14) are designed such that their stiffness in the out-of-plane bending direction is high while they have low stiffness in in-plane directions. The cross-sectional view demonstrated in FIG. 2 presents an exemplary design that yields retaining springs (14) with high stiffness in the out-of-plane bending direction due to a high height to width ratio. On the other hand, the stiffness of the retaining springs (14) in the in-plane directions is minimized due to the small width and a folded structure demonstrated in the schematic view in FIG. 1.

Figure 3:
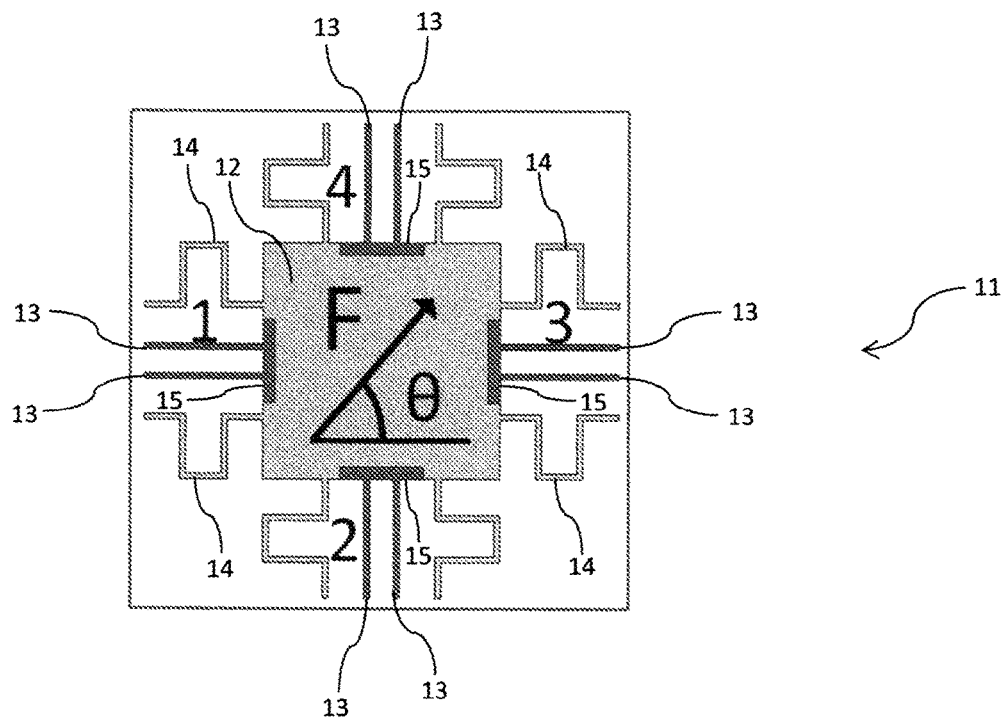
FIG. 3 schematically demonstrates the manner according to which direction of applied force is determined from the ratio of the strains on piezoresistive nanowires.
Figure 4:
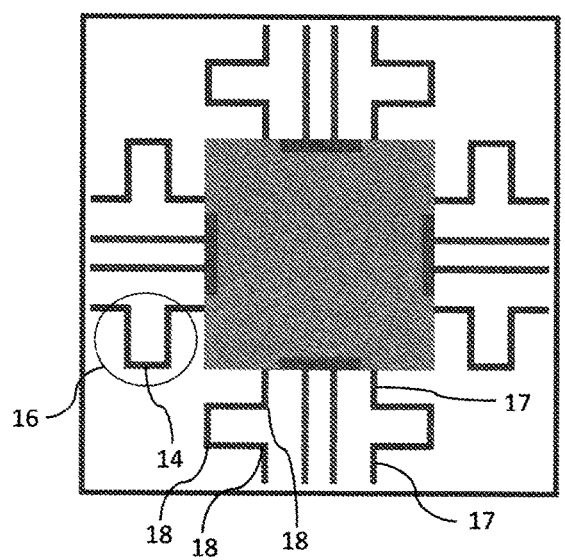
FIG. 4 demonstrates a general schematic view of a MEMS sensor comprising an interaction platform with the folded structure of the retaining springs.

The multi-axis MEMS force sensor (11) described herein is capable of measuring the magnitude and direction of applied in-plane forces. Hence, using an array of sensors, a 2D force vector map can be generated. Current-voltage (I-V) measurements are used to determine the relative change in resistance of the strain-sensitive nanoscale elements (13) as a result of the applied force. The magnitude of the applied force can be calculated using the magnitude of the relative change in resistance. The direction of the applied force, referred to as the angle between the force vector and the positive x-axis, can be determined from the ratio of the strains on strain-sensitive nanoscale elements (13) whose longitudinal axes are perpendicular to each other (FIG. 3).

The strains on nanowire pairs that are on opposing sides of the platform (pairs of nanowires labeled as 1-3, and 2-4 in FIG. 3) are equal in magnitude but have opposite signs:

$\varepsilon 1=-\varepsilon 3$ $\varepsilon 2=-\varepsilon 4$

The angle between the direction of applied force and the positive x-direction can be calculated by:

$\varepsilon 2/\varepsilon 1=\varepsilon 4/\varepsilon 3=\tan\theta$

The overall sensitivity of the MEMS force sensor (1) depends on two major factors: First is the mechanical sensitivity of the device structure which is defined as the ratio of the magnitude of mechanical stress developed in the nanowire to the magnitude of the applied force. The second factor is the sensitivity of the piezoresistive nanowire transducers which is defined as the ratio of the relative change in resistance to the magnitude of applied strain. The MEMS force sensor (11) described herein was designed with the purpose of maximizing these two ratios.

According to the present disclosure, it is established that the mechanical sensitivity of the device structure can be optimized by minimizing the stiffness of the structure, therefore maximizing the stresses and strains on the nanowire for a given magnitude of applied force. The effect of the stiffness of the retaining springs is therefore decisive in the mechanical sensitivity of the device structure. It is established that the magnitude of strain on the nanowire increases as spring width decreases since the stiffness of the spring decreases with decreasing width.

Accordingly, the MEMS force sensor (11) device was designed to include retaining springs (14) with low width and an increased height (FIG. 3). This way, the stiffness of the springs in the in-plane directions is kept low while their stiffness in out-of-plane directions is high enough so that the springs can prevent the out-of-plane bending of the interaction platform (12) significantly. The height to width ratio of the retaining springs (14) is at least greater than 2 and is preferably 5-15.

The sensitivity of the piezoresistors (referred to as the gauge factor) is the ratio of the relative change in resistance of the nanowire to the applied strain. The gauge factor is derived from the constitutive relation describing the piezoresistive effect:

$\Delta R/R = \pi \sigma$

Here, $\Delta R/R$, $\pi$, and $\sigma$ are the relative change in resistance, piezoresistive coefficient, and the applied stress, respectively. Incorporating Hooke's Law into this equation:

$\Delta R/R = (E\pi)\varepsilon$

Here, E is the elastic modulus, and $\varepsilon$ is the applied strain. The product of elastic modulus and piezoresistive coefficient is called the gauge factor, and it is defined as the sensitivity of a piezoresistor:

$G = E\pi$

For a doped single crystal silicon nanowire, the value of the gauge factor depends on the doping type, dopant concentration, and orientation. Regarding the doping type, the options are p-type (doped with Boron) and n-type (doped with Phosphorus or Arsenic). In terms of orientation, crystallographic directions on the (100) plane of single crystal silicon are considered since the MEMS force sensor devices are fabricated on SOI wafers with (100) silicon device layer orientation. On the (100) plane of single crystal silicon, the elastic modulus is maximum along the <110> directions. The piezoresistive coefficient of p-type doped silicon is also maximum along the <110> directions of the (100) plane. These set of material properties are found effective since it is customary in microfabrication processes to align features along <110> directions. Regarding dopant concentration, a value of $10^{17}$ cm$^{-3}$ was selected for the concentration of Boron atoms since the piezoresistive coefficients decrease significantly for dopant concentrations exceeding $10^{18}$ cm$^{-3}$ and dopant concentrations below $10^{17}$ cm$^{-3}$ results in low conductivity and the readout signal amplitudes decrease. In conclusion, the MEMS force sensor (11) device was designed so that the piezoresistive nanowires are oriented along the <110> directions of the (100) plane of single crystal silicon and are doped with Boron atoms at a concentration of $10^{17}$ cm$^{-3}$ in order to maximize the sensitivity of the piezoresistive silicon nanowire transducers.

The multi-axis MEMS force sensor (11) described herein works on the principle of piezoresistive transduction. Piezoresistive silicon nanowires are used to measure the mechanical force applied on the interaction platform (12). The applied force generates a mechanical strain on the nanowires and their resistances change due to the piezoresistive effect. This change in resistance is determined by conducting IV measurements. The current flowing through the strain-sensitive nanoscale elements (13) is monitored while applying constant voltage. The static current, which is the current measured while no force is applied, depends on the applied voltage and the nanowire resistance, based on Ohm's law. The amount of change in measured current when a force is applied to the sensor device depends on the magnitude of force and sensitivity of the device. For the MEMS force sensor (11) design disclosed herein, the predicted values of static current and current change for an applied force of 100 nN were calculated using piezoresistance theory, material properties, and strain values.

According to the disclosure, strain-sensitive nanoscale elements (13) have lengths ranging from 2 μm to 5 μm and widths ranging from 100 nm to 250 nm.

Fabrication of multi-axis MEMS devices are delineated hereinafter: The MEMS force sensors (11) are fabricated on Silicon-On-Insulator (SOI) wafers using CMOS compatible microfabrication technology. Technical specifications of the SOI wafers are shown in Table 1:

TABLE 1

Technical specifications of the SOI wafers used

| | |
| --- | --- |
| Diameter | 100 mm |
| Orientation | (100) |
| Doping type | P-type (Boron) |
| Resistivity | 20 Ωcm-30 Ωcm |
| Device layer thickness | 2 ± 0.5 μm |
| Buried oxide thickness | 2 μm ± 5% |
| Handle layer thickness | 500 ± 10 μm |

First, the strain-sensitive nanoscale elements (13) and metal contact pads were doped by ion implantation with Boron ions to achieve a doping concentration of $10^{17}$ cm$^{-3}$. A second doping by ion implantation was performed to increase conductivity in the ohmic contact pads and unstrained parts of the nanowire bridge. These regions were doped with Boron ions to achieve a doping concentration of $10^{20}$ cm$^{-3}$. After the ion implantation process is completed, a drive-in step is carried out to achieve thermally induced vertical diffusion of the implanted dopant ions through the entire device layer thickness.

Next, the sensor structure is defined by two successive silicon etch steps using reactive ion etching (RIE). First, the entire geometry is defined by RIE etching of the 2 μm thick silicon device layer. A second RIE etch step is performed to reduce the thickness of the nanowire bridge structures from 2 μm to 0.25 μm.

After the doping and silicon etching processes are completed, metallization step is carried out. The entire wafer surface is coated with a thin (~30 nm) layer of Titanium first, and then an Aluminum film is deposited using sputtering. The metal films are patterned by photolithography and etching.

The next process is the deposition and patterning of a protection layer. The protection layer is required since metals and buried silicon dioxide need to be protected during the HF vapor release etch. Polyimide is chosen as a protection layer since it can be deposited, patterned, and removed with ease. The surface of the wafer is coated with a polyimide film and the film is patterned by photolithography to allow access to the oxide that is to be etched in the release process.

Next step is the anisotropic etching of the buried oxide with Freon RIE. This step ensures that the duration of HF vapor release is minimized since a portion of the oxide is removed and the surface area of the oxide is increased. After Freon RIE etching of the buried oxide, wafer dicing is performed to cut out the dies from the wafer.

After RIE etching of the buried oxide and dicing, HF vapor release is performed. The dies are exposed to vapor phase HF which etches the buried oxide underneath the platform, springs, and nanowires, allowing them to be suspended freely.

The final step of the microfabrication process flow is the removal of the polyimide protection layer to allow access to the metal contact pads which are going to be used to wire bond the die on a PCB substrate. The removal of the polyimide film is achieved by $O_2$ plasma ashing.

The microelectromechanical systems (MEMS) force sensor (11) described herein utilizes strain-sensitive nanoscale elements (13) as electromechanical transducers. The strain-sensitive nanoscale elements (13) form a bridge between the interaction platform (12) and respective anchoring means. Hence, the external force applied to the interaction platform (12) is transmitted directly onto the strain-sensitive nanoscale elements (13). It is therefore to be noted that the strain-sensitive nanoscale elements (13) being directly subject to the external force ensure a more sensitive measurement. Enhancement of the sensitivity is provided particularly due to the fact that the measurement is effected not by bending of the strain-sensitive nanoscale elements (13) but by the straining activity thereof in a configuration where the retaining springs (14) substantially prevent out-of-plane bending direction movements while allowing in-plane direction movements.

It is also further to be noted that due to the fact that the measurements are directly effected by means of the strain-sensitive nanoscale elements (13), a structure dimensionally adapted to interact with a single biological cell is obtainable. The microelectromechanical system (MEMS) sensor device can also involve a plurality of MEMS force sensors (11) to interact with a single biological cell performing contact force measurements at different parts thereof or can be structured as an array of MEMS force sensors (11) interacting with a plurality of cells.

Therefore, using the strain-sensitive nanoscale elements (13) as the main sensing elements is one key aspect contrary to the situation where piezoresistors are embedded or attached on a larger mechanical structure such as a cantilever beam, a double-clamped beam, or a membrane to be then used as the mechanical sensing element. Utilizing piezoresistive nanowires as the main sensing elements enables design and microfabrication of highly miniaturized sensors capable of high-resolution force measurement. An array of highly miniaturized and high-resolution force sensors makes it possible to perform contact force measurements from multiple locations on a single biological cell. The microelectromechanical systems (MEMS) force sensor (11) described herein has dimensions of 20 μm×20 μm fabricated on a 2 μm thick Silicon layer and can be used to measure forces on the order of 100 nN.

In a nutshell, a microelectromechanical system (MEMS) sensor device comprising at least one microelectromechanical system sensor (11) to characterize intracellular dynamics and behavior of a living biological cell so as to quantitatively measure the mechanical stiffness and strength thereof, said microelectromechanical system sensor (11) being responsive to mechanical force changes during said cell's contraction, migration, proliferation and differentiation.

In one embodiment, said microelectromechanical system (MEMS) sensor comprises an interaction platform in the form of a mechano-sensitive platform to have a direct contact with said living biological cell and to measure forces generated by said cell by way of measurement of displacements of said interaction platform (12) and said microelectromechanical system (MEMS) sensor (11) comprises strain-sensitive nanoscale elements (13) in the form of electromechanical transducer elements sensing mechanical force applied by said cell in direct contact with said living biological cell.

In a further embodiment, said interaction platform (12) is a rectangular planar surface medium, each edge of which is connected with at least two strain-sensitive nanoscale elements (13) in the form of piezoresistive nanowires. The rectangular form with two nanoscale elements at each edge ensures measurement uniformity.

In a further embodiment, said at least two strain-sensitive nanoscale elements (13) connected with the edge of the interaction platform (12) are connected to each other through a conductive edge line (15) at least partially extending along said edge. The two nanoscale elements being connected ensures measurability of the mechanical force being applied.

In a further embodiment, said at least two strain-sensitive nanoscale elements (13) connected with the edge of said interaction platform (12) extend between the interaction platform (12) and a respective anchoring means associated with said edge.

In a further embodiment, said interaction platform (12) is suspended by retaining springs (14) extending between each edge of the interaction platform (12) and a respective anchoring means associated with said edge.

In a further embodiment, said strain-sensitive nanoscale elements (13) are made of doped single crystal silicon.

In a further embodiment, said retaining springs (14) are configured such that their stiffness in the out-of-plane bending direction of said interaction platform (12) is higher than that in in-plane directions whereby the motion of the interaction platform (12) is constrained to in-plane displacements.

In a further embodiment, width of said retaining springs (14) is configured in a decreased manner so as to obtain a lower in plane stiffness of said retaining springs (14) and an increased magnitude of strain on the strain-sensitive nanoscale elements (13).

In a further embodiment, height to width ratio of the retaining springs (14) is at least greater than 2 and is preferably between 5 and 15.

In a further embodiment, electric current flow through a strain-sensitive nanoscale element (13) is measured to proportionally calculate in-plane force gradients being exerted parallel to the surface of said interaction platform (12).

In a further embodiment, change in resistance of the strain-sensitive nanoscale element (13) is monitored by I-V measurements to determine the relative change in resistance of the rain-sensitive nanoscale element (13) and magnitude of the force applied by a living biological cell.

In a further embodiment, the current flowing through the strain-sensitive nanoscale element (13) is monitored while applying constant voltage.

In a further embodiment, direction of the applied force is determined from the ratio of the strains on strain-sensitive nanoscale elements (13) whose longitudinal axes are perpendicular to each other.

In a further embodiment, the strain-sensitive nanoscale elements (13) are oriented along the <110> directions of the (100) plane of single crystal silicon and are doped with Boron atoms.

In a further embodiment of the present invention, the retaining springs (14) are provided with a folded structure (16) disposed between two linear spring portions (17). The stiffness of the retaining springs (14) in the in-plane directions is minimized due to the small width and the folded structure (16) having folding lines (18).

In a further embodiment, the folded structure (16) disposed between two aligned spring portions (17) comprises at least two folding lines (18) between two linear spring portions (17).

In a further embodiment, the two linear spring portions (17) at both ends of the folded structure (16) extend in an aligned manner, contributing to the minimization if the stiffness of the retaining springs (14) in the in-plane directions.

In a further embodiment, the microelectromechanical system (MEMS) sensor device comprises an array of microelectromechanical system (MEMS) sensors (11) to generate a 2D force vector map by which array type parallel time-domain multiplex analysis is conducted.

The invention claimed is:

1. A microelectromechanical system (MEMS) sensor device comprising: a microelectromechanical system sensor to characterize intracellular dynamics and behavior of a living biological cell so as to quantitatively measure a mechanical stiffness and a strength thereof, said microelectromechanical system sensor responsive to mechanical force changes during said living biological cell's contraction, migration, proliferation and differentiation;

said microelectromechanical system (MEMS) sensor comprising an interaction platform in a form of a mechano-sensitive platform configured to have direct contact with said living biological cell and to measure forces generated by said living biological cell by way of measuring displacements of said interaction platform, wherein said interaction platform is a rectangular planar surface medium, an edge of which is connected with at least two strain-sensitive nanoscale elements in the form of piezoresistive nanowires, wherein said interaction platform is suspended by retaining springs extending between the edge of the interaction platform and a respective anchor associated with said edge; and, said microelectromechanical system (MEMS) sensor comprises strain-sensitive nanoscale elements in a form of electromechanical transducer elements configured to sense mechanical force applied by said cell in direct contact with said mechano-sensitive platform.

2. A microelectromechanical system (MEMS) sensor device as set forth in claim 1, wherein said at least two strain-sensitive nanoscale elements connected with the edge of the interaction platform are connected to each other through a conductive edge line at least partially extending along said edge.

3. A microelectromechanical system (MEMS) sensor device as set forth in claim 1, wherein said at least two strain-sensitive nanoscale elements connected with the edge of said interaction platform extend between the interaction platform and a respective anchor associated with said edge.

4. A microelectromechanical system (MEMS) sensor device as set forth in claim 1, wherein said strain-sensitive nanoscale elements are made of doped single crystal silicon.

5. A microelectromechanical system (MEMS) sensor device as set forth in claim 1, wherein said retaining springs are configured such that a stiffness in an out-of-plane bending direction of said interaction platform is higher than that in an in-plane direction whereby the motion of the interaction platform is constrained to in-plane displacements.

6. A microelectromechanical system (MEMS) sensor device as set forth in claim 5, wherein a width of said retaining springs is configured in a decreased manner so as to obtain a lower in plane stiffness of said retaining springs and an increased magnitude of strain on the strain-sensitive nanoscale elements.

7. A microelectromechanical system (MEMS) sensor device as set forth in claim 5, wherein a height to width ratio of the retaining springs is at least greater than 2 and is preferably between 5 and 15.

8. A microelectromechanical system (MEMS) sensor device comprising: a microelectromechanical system sensor to characterize intracellular dynamics and behavior of a living biological cell so as to quantitatively measure a mechanical stiffness and a strength thereof, said microelectromechanical system sensor responsive to mechanical force changes during said living biological cell's contraction, migration, proliferation and differentiation;
    said microelectromechanical system (MEMS) sensor comprising an interaction platform in a form of a mechano-sensitive platform configured to have direct contact with said living biological cell and to measure forces generated by said living biological cell by way of measuring displacements of said interaction platform and,
    said microelectromechanical system (MEMS) sensor comprises strain-sensitive nanoscale elements in a form of electromechanical transducer elements configured to sense mechanical force applied by said cell in direct contact with said mechano-sensitive platform and, wherein electric current flowing through a strain-sensitive nanoscale element is measured to proportionally calculate in-plane force gradients being exerted parallel to the surface of said interaction platform.

9. A microelectromechanical system (MEMS) sensor device as set forth in claim 8, wherein a change in resistance of the strain-sensitive nanoscale element is monitored by current—voltage measurements to determine a relative change in resistance of the strain-sensitive nanoscale element and a magnitude of the force applied by a living biological cell.

10. A microelectromechanical system (MEMS) sensor device as set forth in claim 9, wherein the current flowing through the strain-sensitive nanoscale element is monitored while constant voltage is applied.

11. A microelectromechanical system (MEMS) sensor device as set forth in claim 1, wherein a direction of the applied force is determined from a ratio of the strains on strain-sensitive nanoscale elements whose longitudinal axes are perpendicular to each other.

12. A microelectromechanical system (MEMS) sensor device as set forth in claim 4, wherein the strain-sensitive nanoscale elements are oriented along directions of a plane of single crystal silicon and are doped with Boron atoms.

13. A microelectromechanical system (MEMS) sensor device as set forth in claim 1, wherein the retaining springs are provided with a folded structure disposed between two linear spring portions.

14. A microelectromechanical system (MEMS) sensor device as set forth in claim 13, wherein the folded structure disposed between two aligned spring portions comprises at least two folding lines between two linear spring portions.

15. A microelectromechanical system (MEMS) sensor device as set forth in claim 13, wherein the two linear spring portions are disposed at both ends of the folded structure and extend in an aligned manner.

16. A microelectromechanical system (MEMS) sensor device as set forth in claim 1, wherein the microelectromechanical system (MEMS) sensor device comprises an array of microelectromechanical system (MEMS) sensors to generate a 2D force vector map to conduct array type parallel time-domain multiplex analysis.

17. A microelectromechanical system (MEMS) sensor device comprising: a microelectromechanical system sensor to characterize intracellular dynamics and behavior of a living biological cell so as to quantitatively measure a mechanical stiffness and a strength thereof, said microelectromechanical system sensor responsive to mechanical force changes during said living biological cell's contraction, migration, proliferation and differentiation;
    said microelectromechanical system (MEMS) sensor comprising an interaction platform in a form of a mechano-sensitive platform configured to have direct contact with said living biological cell and to measure forces generated by said living biological cell by way of measuring displacements of said interaction platform, wherein said interaction platform is suspended by retaining springs extending between the edge of the interaction platform and a respective anchor associated with said edge; and
    said microelectromechanical system (MEMS) sensor comprises strain-sensitive nanoscale elements in a form of electromechanical transducer elements configured to sense mechanical force applied by said cell in direct contact with said mechano-sensitive platform.

* * * * *